United States Patent [19]

Wolf et al.

[11] Patent Number: 4,934,519
[45] Date of Patent: Jun. 19, 1990

[54] PROCESS FOR WORKING UP CRUDE LIQUID VINYL ACETATE

[75] Inventors: Gunter Wolf, Leverkusen; Hubert Lauer, Dormagen; Wulf Schwerdtel, Leverkusen, all of Fed. Rep. of Germany

[73] Assignee: Bayer Aktiengesellschaft, Leverkusen, Fed. Rep. of Germany

[21] Appl. No.: 750,815

[22] Filed: Jun. 28, 1985

Related U.S. Application Data

[63] Continuation of Ser. No. 320,787, Nov. 12, 1981, abandoned.

[30] Foreign Application Priority Data

Aug. 13, 1981 [DE] Fed. Rep. of Germany ....... 3131981

[51] Int. Cl.$^5$ .......................... B01D 3/36; C07C 67/54
[52] U.S. Cl. ......................... 203/96; 203/97; 203/DIG. 10; 203/DIG. 19; 560/248
[58] Field of Search ................ 203/92, 93, 96, 97, 203/76, 79, 83, 85, 14, DIG. 10, DIG. 19; 560/248; 562/608

[56] References Cited

U.S. PATENT DOCUMENTS

| | | | |
|---|---|---|---|
| 2,681,306 | 6/1954 | Kemp et al. | 203/96 |
| 3,182,006 | 5/1965 | Fruhwirth | 203/DIG. 10 |
| 3,404,177 | 10/1968 | Baba et al. | 203/14 |
| 3,458,406 | 7/1969 | Fisher et al. | 560/248 |
| 3,692,636 | 9/1972 | Huguet | 203/DIG. 10 |
| 3,905,875 | 9/1965 | Kronig et al. | 203/14 |
| 4,229,261 | 10/1980 | Heck et al. | 203/DIG. 10 |
| 4,438,870 | 4/1969 | Roscher et al. | 203/14 |

OTHER PUBLICATIONS

Horsely; *Azeotropic Data II*, Advances in Chemistry Series 116, (AMCS, 1973), p. 20.

*Primary Examiner*—Wilbur Bascomb
*Attorney, Agent, or Firm*—Sprung Horn Kramer & Woods

[57] ABSTRACT

An improved process for working-up crude liquid vinyl acetate which contains vinyl acetate, acetic acid, water, and ethyl acetate, possibly together with small amounts of other impurities, by distillation is disclosed, wherein a mixture essentially containing vinyl acetate and water is obtained as the top product and essentially acetic acid is obtained as the bottom product, and a sidestream, in which ethyl acetate is concentrated is removed. According to the process the top product is condensed and, after phase separation, a portion of the vinyl acetate phase is recycled as reflux into the distillation. The improved process involves the introduction of water above the point of introduction of the crude vinyl acetate. Preferably, the water is introduced in an amount which is not greater than the amount required to achieve a maximum water content in the vapors leaving the distillation at the top.

7 Claims, 1 Drawing Sheet

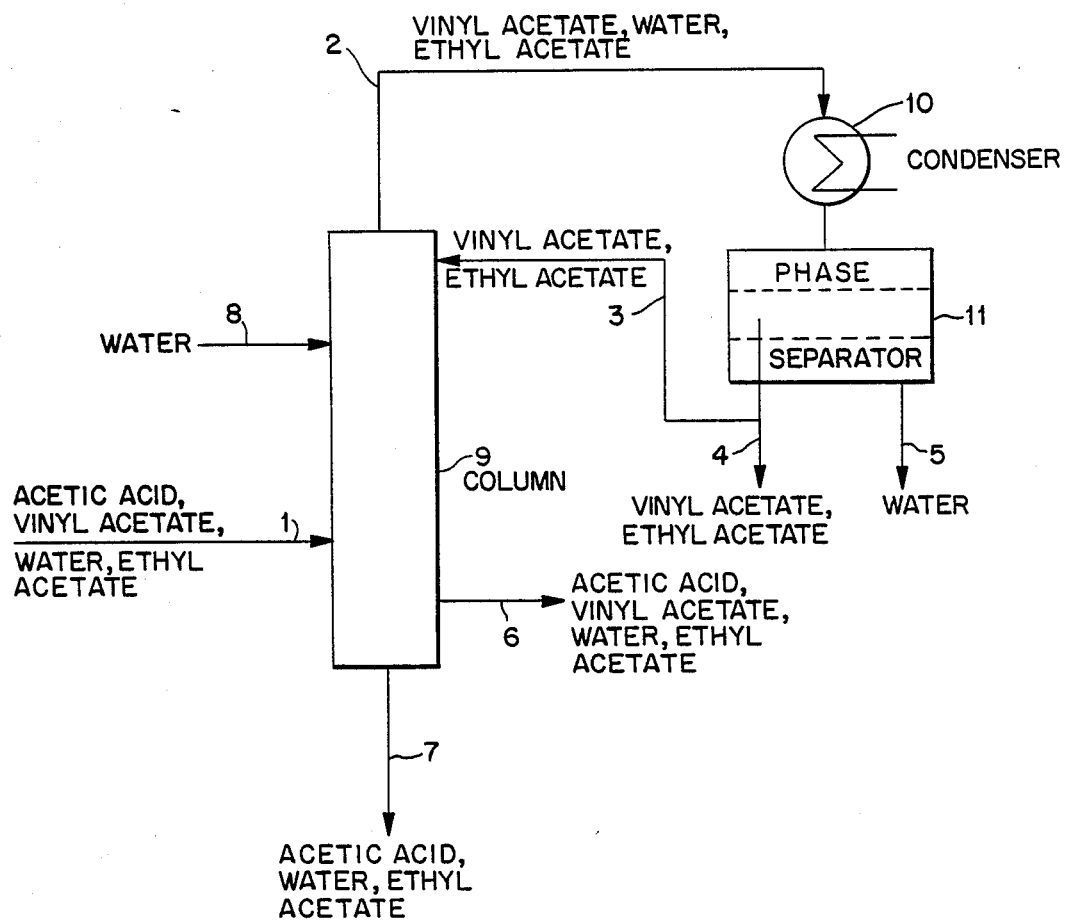

PROCESS FOR WORKING UP CRUDE LIQUID VINYL ACETATE

This is a continuation of application Ser. No. 320,787, filed Nov. 12, 1981, now abandoned.

BACKGROUND OF THE INVENTION

1. Field of the invention

The present invention relates to a process for working up crude liquid vinyl acetate which contains acetic acid and water and also ethyl acetate and, if appropriate, further impurities.

2. Discussion of prior art

Processes for the manufacture of vinyl acetate frequently yield a liquid crude vinyl acetate which essentially contains acetic acid and water and also ethyl acetate and, if appropriate, further impurities. A product of this type can be obtained, for example, in the manufacture of vinyl acetate by reacting ethylene with acetic acid and oxygen, in the gas phase, at elevated temperature and under normal or elevated pressure, in the presence of a catalyst, the gases leaving the reactor being cooled and/or washed with acetic acid. This type of manufacture of vinyl acetate is generally carried out with excess acetic acid, the unreacted acetic acid being recycled into the vinyl acetate manufacture.

A method of working up crude liquid vinyl acetate, accessible by such manufacturing processes, which still contains acetic acid and water and also ethyl acetate and, if appropriate, further impurities, is described in German Auslegeschrift 1,768,412. In this process, the crude vinyl acetate is azeotropically distilled, the major part of the water, together with vinyl acetate, is drawn off at the top by recycling the vinyl acetate obtainable by condensation and phase separation of the top product, and vinyl acetate is recycled in an amount such that an acetic acid which contains about 0.5 to 6% by weight of water is obtained as the bottom product. If appropriate, a liquid sidestream, in which ethyl acetate is concentrated, can be removed from this distillation. In this process, the water content of the top vapours from the distillation is about 3.4% by weight (compare the repetition of the process of German Auslegeschrift 1,768,412. carried out according to Example 1). The vinyl acetate obtainable after condensation and phase separation of the gaseous top product contains about 200 to 500 ppm by weight of ethyl acetate.

Another known process for working up crude vinyl acetate is described in German Pat. No. 1,282,014 and German Pat. No. 1,668,063. In this process, the water, as an azeotropic mixture, and the by-products boiling at a lower temperature than vinyl acetate are distilled overhead, and the virtually anhydrous bottom product is distilled in a second distillation column, vinyl acetate being removed at the top of the second distillation column, at least the major part of the by-products boiling at a higher temperature than vinyl acetate being removed from one or more concentration zones between the top and the bottom, and the acetic acid and, if appropriate, the remainder of the by-products being removed below the lowest concentration zone or as the bottom product. The vinyl acetate obtained in the first column after condensation and phase separation is generally recycled completely into the first column, and vinyl acetate is only removed from the top of the second column. No information on the water content of the gaseous top product of the first column is given, and the ethyl acetate content in the vinyl acetate separated off is about 1,000 ppm.

German Offenlegungsschrift 2,943,985 describes a process for the separation of water from mixtures with vinyl acetate and acetic acid, in which two different mixtures of crude vinyl acetate are introduced into a distillation column at various points. The top product can then contain about 3 to 5% by weight of water. In cannot be inferred from this German Offenlegungsschrift whether crude vinyl acetate containing ethyl acetate can be worked up in this way and what contents of ethyl acetate are then present in the vinyl acetate separated off.

Finally, German Auslegeschrift 1618240 describes a method for separation of ethyl acetate from vinyl acetate, in which extractive distillation is carried out using water as the entrainer. In this process, however, the vinyl acetate used does not contain significant amounts of water and/or acetic acid.

SUMMARY OF THE INVENTION

A process has now been found for working up crude liquid vinyl acetate which contains acetic acid and water and also ethyl acetate and, if appropriate, further smaller amounts of impurities, by distillation, a mixture essentially containing vinyl acetate and water being obtained as the top product and essentially acetic acid being obtained as the bottom product, and a sidestream, in which ethyl acetate is concentrated, being removed, and the top product being condensed and, after phase separation, part of the vinyl acetate phase being recycled as reflux into the distillation, which process is characterised in that water is introduced into the distillation, above the point of introduction of the crude liquid vinyl acetate. Preferably the water is introduced in an amount which is not greater than the amount required to achieve a maximum water content in the vapours leaving the distillation at the top.

BRIEF DESCRIPTION OF THE DRAWING

The drawing schematically depicts the inventive process.

DETAILED DESCRIPTION OF THE INVENTION

A suitable vinyl acetate for use in the process according to the invention is, for example, crude liquid vinyl acetate which contains about 12 to 30% by weight of vinyl acetate, about 3 to 10% by weight of water, about 0.05 to 0.2% by weight of ethyl acetate, and acetic acid to make up to 100% by weight. Further impurities, for example diacetates, polymers, acetaldehyde and/or methyl acetate, can also be present in small amounts, for example in amounts of less than 0.5% by weight in each case. Such impurities may have been formed in the vinyl acetate manufacture or may have already been introduced into the vinyl acetate manufacture together with the starting materials.

A crude liquid vinyl acetate suitable for use in the process according to the invention can be obtained in a variety of ways. For example, ethylene, oxygen and acetic acid can be reacted in a known manner, in the gas phase, at elevated temperature and under normal or elevated pressure, on catalysts containing a noble metal or noble metal compounds, and the gases resulting from this reaction can be cooled and/or washed, for example with acetic acid or wash liquids containing acetic acid, and the crude liquid vinyl acetate obtainable in this way can be used in the process according to the invention.

The crude liquid vinyl acetate is introduced into a distillation column. Examples of suitable distillation columns are those which contain 50 to 90 trays, preferably 55 to 85 trays, and are operated under normal pressure or a slightly elevated pressure, for example under an absolute pressure of 1 to 5 bars, preferably under normal pressure. In this process, the crude liquid vinyl acetate can be introduced into the column, for example, at a point which is in the central region of the column, preferably between the centre and the bottom third of the column. The column is operated in such a way that a gaseous mixture essentially containing vinyl acetate and water is obtained as the top product and essentially acetic acid is obtained as the bottom product, and a sidestream, in which ethyl acetate is concentrated, is removed. The column is preferably operated in such a way that a water content of 0.5 to 6% by weight is maintained in the acetic acid drawn off at the bottom, and that the sidestream removed below the feed of the starting mixture contains, for example, up to 8% by weight of ethyl acetate in addition to varying amounts of vinyl acetate, acetic acid and water. This sidestream can be removed as a liquid or a gas. Preferably, this sidestream is removed in liquid form. The top product of the column is condensed and, after phase separation, part of the vinyl acetate phase is recycled as reflux into the distillation column. In this process, the proportion of the recycled vinyl acetate is regulated in such a way that the desired water content, for example in the range from 0.5 to 6% by weight, is established at the bottom of the column. In general, a reflux ratio (ratio of vinyl acetate recycled to vinyl acetate removed) in the range of from 3:1 to 8:1 is advantageous for this purpose. The unrecycled vinyl acetate is separated off and, if required, can be purified still further. The bottom product obtained in the distillation, which generally contains more than 90% by weight of acetic acid, can be recycled into the process for the manufacture of vinyl acetate, if appropriate after the separation of impurities, for example polymers.

In this procedure, virtually all the vinyl acetate introduced with the crude liquid vinyl acetate, and part of the water introduced with the crude liquid vinyl acetate, are removed at the top. The procedure described hitherto, including the further purification, to be carried out if appropriate, of the vinyl acetate separated off and of the acetic acid obtained at the bottom, is known, for example, from German Auslegeschrift 1,768,412.

The step to be taken, according to the present invention, in this working-up of crude liquid vinyl acetate consists in introducing water, above the point of introduction of the crude liquid vinyl acetate, preferably in an amount which is not greater than the amount required to achieve a maximum water content in the vapours leaving the distillation at the top.

Only small amounts of water, for example 0.1 to 1% by weight, relative to the crude liquid vinyl acetate used, which are introduced in this way, cause an increase in the water content of the vapours leaving the distillation at the top, and cause a reduction in the ethyl acetate content of the vinyl acetate separated from the top product of the distillation. If more water is introduced in this way, these effects occur to a greater extent until a maximum water content is achieved in the vapours leaving the distillation at the top. It is known that the vinyl acetate/water azeotrope can have a maximum content of 7.3% by weight of water (compare Advances in Chemistry, Series 116, Azeotropic Data III, American Chemical Society, Washington D.C., 1973).

However, in general, this value cannot quite be achieved when carrying out the process according to the invention in practice. The maximum water content in the vapours leaving the distillation at the top, which can be achieved when carrying out the process according to the invention in practice, is about 6.8% by weight. Preferably, water is introduced, in the manner according to the invention, in just the amount which corresponds to a water content of 6.7 to 6.9% by weight in the gases leaving the distillation at the top. In this way, the effects obtainable with the process according to the invention are achieving in the optimum manner.

If more water is introduced that is required to achieve a maximum water content in the vapours leaving the distillation at the top, the water content of the vapours leaving the distillation at the top naturally does not increase further, the reduction in the ethyl acetate content in the vinyl acetate separated from the top product of the distillation is maintained but the water content at the bottom of the column increases. In certain cases it is of advantage when the latter does not occur, for example, a given water balance in a given vinyl acetate manufacturing process may be disturbed by an increasing water content in the bottom product of the distillation. Therefore in a preferred embodiment of the present invention the water is introduced in an amount not greater than the amount required to achieve a maximum water content in the vapours leaving the distillation at the top.

The amount of water to be introduced according to the invention is relatively small. It can be, for example, 0.1 to 5% by weight, relative to the crude liquid vinyl acetate used. This amount is preferably 0.5 to 4% by weight and particularly preferably 0.8 to 3% by weight. The amount of water which is necessary, in a concrete individual case, to achieve the highest possible water content in the gases leaving the distillation at the top can be determined, if appropriate, by simple experiments. This amount of water depends, for example, on how much water and vinyl acetate are present in the crude vinyl acetate used.

The water to be added according to the invention can be introduced into the distillation in liquid form or as steam. The water is introduced above the point of introduction of the crude liquid vinyl acetate. Water introduced below the feed of the crude liquid vinyl acetate, or with the latter, does not improve the water removal in the distillation and does not lower the ethyl acetate content of the vinyl acetate separated from the top product of the distillation. It is particularly advantageous to carry out the introduction of water, according to the invention, a little above the point of introduction of the crude liquid vinyl acetate, for example 2 to 5 trays above the point of introduction of the crude liquid vinyl acetate.

The procedure according to the invention has the following advantages:

The water removal in the distillation is improved by higher water content in the vapours leaving the distillation at the top. This means that it is possible either to obtain a water content which is up to 10% (relative) smaller than hitherto, with unchanged vinyl acetate reflux, at the bottom, or to achieve identical water content at the bottom as hitherto, with a smaller vinyl acetate reflux, and/or from a crude vinyl acetate containing more water, and/or in a shorter column.

The vinyl acetate/ethyl acetate separation is improved. This means that it is possible either to obtain a vinyl acetate separated off which contains up to about 705 less ethyl acetate that hitherto, with unchanged vinyl acetate reflux, or to achieve the same ethyl acetate content as hitherto, in the vinyl acetate separated off, with a smaller vinyl acetate reflux, and/or from a crude vinyl acetate containing more ethyl acetate, and/or in a shorter distillation column.

Of course, the present invention also makes it possible to obtain a combination of these advantages, for example a reduced vinyl acetate reflux and a lowering of the water content at the bottom.

It is particularly advantageous that the improvements achievable according to the invention are obtained without increasing the outlay for the distillation, for example as regards the number of trays, the reflux amounts and the energy requirement.

It is decidedly surprising that the additional introduction of water, according to the present invention, makes it possible to improve the water removal effect and the vinyl acetate/ethyl acetate separation. In the methods known hitherto for working up crude liquid vinyl acetate, in which vinyl acetate and water are distilled at the top, there is already sufficient water present to be able theoretically to achieve a water content of about 7% by weight in the vapours leaving the distillation at the top. Despite this, attempts to achieve such water contents in the vapours leaving the distillation at the top have hitherto been unsuccessful in practice. For example, it is indicated in German Offenlegungsschrift 2,943,985 that this water content is about 3 to 5% by weight, and in the procedure corresponding to German Auslegeschrift 1,768,412, it is about 3.4% by weight (compare the repetition of the process of German Auslegeschrift 1,768,412, carried out according to Example 1). As is known, the vinyl acetate/ethyl acetate separation is a difficult task because of the very similar boiling points of the two substances (ethyl acetate: 77° C., vinyl acetate: 73° C.). It is also surprising, in particular, that these two effects i.e. improved water removal and improved vinyl acetate/ethyl acetate separation, can be achieved by taking one step, namely the introduction of water according to the invention.

Referring to the drawing, in which like parts are designated by like reference numerals, a feed containing acetic acid, vinyl acetate, water and ethyl acetate enter via conduit 1 into column 9. Water is introduced into column 9 above the feed via conduit 8. The bottoms from column 9, containing acetic acid and water and ethyl acetate, exit the column 9 via conduit 7. Towards the bottom of column 9, a stream containing acetic acid, vinyl acetate, water and ethyl acetate are withdrawn via conduit 6. Vinyl acetate, water and ethyl acetate exit overhead from column 9 in conduit 2. Such overhead then passes through condenser 10 into phase separator 11. Water exits the phase separator 11 via conduit 5. Vinyl acetate and ethyl acetate exit phase separator 11 via conduit 4, a sidestream of which enters column 9 via conduit 3.

The following example illustrate the process according to the invention without in any way limiting it.

EXAMPLES

The essential features of the examples given below are summarized in Table 1.

EXAMPLE 1

(Comparison example, procedure corresponding to German Auslegeschrift 1,768,412)

1,557 g per hour of a feed mixture of the following composition:

| vinyl acetate | 17.24% by weight |
| --- | --- |
| ethyl acetate | 0.14% by weight |
| water | 3.83% by weight |
| acetic acid | 78.79% by weight | were introduced into a 65-tray glass laboratory bubble-tray column at the 25th tray.

The top product was condensed, cooled to 35° C. and passed into a phase separator. 1,056 g/hour of the vinyl acetate phase were pumped to the top of the column as reflux and the remainder was removed. The composition of the vinyl acetate separated off was as follows:

| ethyl acetate | 353 ppm by weight |
| --- | --- |
| water | 1.2% by weight |
| vinyl acetate | remainder |

The amount of water removed from the phase separator was 30.3 g/hour and the water content of the top vapour of the column was 3.37% by weight.

A liquid sidestream having the following composition:

| vinyl acetate | 22.34% by weight |
| --- | --- |
| ethyl acetate | 1.83% by weight |
| water | 4.52% by weight |
| acetic acid | 71.31% by weight | was removed from the 8th tray of the column in an amount of 29.5 g/hour.

The amount of product removed from the bottom of the column was 1,218 g/hour and had the following composition:

| vinyl acetate | 0.047% by weight |
| --- | --- |
| ethyl acetate | 0.108% by weight |
| water | 2.07% by weight |
| acetic acid | remainder |

EXAMPLES 2 to 5

In these examples, the same column as in Example 1 was operated under the same conditions as in Example 1. In addition, water was introduced into the column in the following manner:

Example 2: 15 g/hour at the 40th tray of the column
Example 3: 30 g/hour at the 40th tray of the column
Example 4: 40 g/hour at the 40th tray of the column
Example 5: 40 g/hour at the 30th tray of the column The results obtained are summarized in Table 1.

It can be seen from this that, as a result of the introduction of water according to the invention, the water content of the bottom product is lowered and the ethyl acetate content of the vinyl acetate drawn off at the top drops very considerably. Furthermore, is can be seen that these effects increase on increasing the amount of water and on introducing the water at a lower tray.

It can also be seen from Table 1 that the amount of water removed from the phase separator is always greater than the sum of following two amounts of water: 1) the amount which is removed without the water feed according to the invention (compare Comparison Example 1) and 2) the amount additionally fed in according to the invention. This clearly shows that not only is the total amount of water fed in according to the invention removed at the top, but also further proportions of water originating from the feed mixture are removed.

removed at the top is small and the ethyl acetate content of the top product is only insignificantly reduced.

TABLE 1

| Example | Reflux g/hour | Water feed g/hour | Water feed %* | Water feed Tray | Water content (% by weight) of the bottom product | Water content (% by weight) of the top vapour | Water from phase separator g/hour | Ethyl acetate in the organic top product ppm by weight |
|---|---|---|---|---|---|---|---|---|
| 1** | 1,056 | — | — | — | 2.07 | 3.4 | 30.3 | 353 |
| 2 | 1,056 | 15 | 0.96 | 40 | 1.89 | 4.6 | 49.4 | 272 |
| 3 | 1,056 | 30 | 1.9 | 40 | 1.84 | 5.7 | 66.7 | 195 |
| 4 | 1,056 | 40 | 2.5 | 40 | 1.80 | 6.4 | 73.2 | 150 |
| 5 | 1,056 | 40 | 2.5 | 30 | 1.78 | 6.4 | 73.5 | 130 |
| 6 | 900 | 40 | 2.5 | 30 | 2.1 | 6.7 | 69.2 | 152 |
| 7 | 1,056 | 50 | 3.2 | 30 | 2.3 | 6.8 | 77.5 | 133 |
| 8** | 1,056 | 40 | 2.5 | 25 | 4.68 | 3.9 | 38.0 | 335 |

*Percentages by weight, relative to vinyl acetate mixture used
**Examples 1 and 8 are not according to the invention

EXAMPLE 6

The same column as in Example 1 was operated under the same conditions as indicated in Example 1. Water was additionally fed into the column at a rate of 40 g/hour at the 30th tray (as in Example 5).

As distinct from the previous examples, the reflux (compare Table 1) was reduced until the bottom product of the column had virtually the same water content as in Example 1 (without the introduction of water according to the invention). It can be seen that, with the procedure according to the invention, the ethyl acetate content of the top product is very considerably lower, even with reduced reflux.

EXAMPLE 7

The procedure of Example 5 was followed, but 50 g/hour of water instead of 40 g/hour of water were fed in at the 30th tray of the column. This is more water than is necessary to form a water content of 6.8% by weight in the top vapour. The excess amount of water fed in is found again in the bottom product and increases the water content thereof. The ethyl acetate content of the top product is also very greatly reduced with this procedure.

EXAMPLE 8

(for comparison)

The same column as in Example 1 was operated under the same conditions as in Example 1.

Water was additionally fed into the column at a rate of 40 g/hour at the 25th tray, that is to say together with the vinyl acetate feed mixture. It can be seen from Table 1 that, with this procedure, the water content at the bottom greatly increases and the major part of the water additionally introduced is thus removed at the bottom of the column, whilst the amount of water additionally

We claim:

1. In a process for working up crude liquid vinyl acetate by distillation, said crude vinyl acetate containing vinyl acetate, acetic acid, water, and ethyl acetate, wherein a mixture essentially containing vinyl acetate and water is obtained as a vapor in a top product, essentially acetic acid is obtained as a bottom product, and a sidestream, in which ethyl acetate is concentrated, is removed, the top product is condensed and, after phase separation, a portion of the vinyl acetate phase is recycled as reflux into the distillation, the improvement which comprises introducing water above the point of introduction of the crude vinyl acetate, said crude vinyl acetate being introduced at a point between the center and bottom third of a distillation column having 50 to 90 trays, said crude liquid vinyl acetate to be worked up containing 12 to 30% by weight of vinyl acetate, 3 to 10% by weight of water, 0.05 to 0.2% by weight of ethyl acetate, and acetic acid to make up 100%, said water being introduced 2 to 5 trays above the point of introduction of the crude liquid vinyl acetate, said water being introduced in an amount which is not greater than the amount required to achieve a maximum water content in the vapors leaving the distillation in the top product, said bottom product containing 0.5 to 6% by weight of water, and said top product containing 133 to 272 ppm of ethyl acetate.

2. A process according to claim 1, wherein crude liquid vinyl acetate additionally contains diacetates, polymers, acetaldehyde and/or methyl acetate, in amounts of less than 0.5% by weight in each case.

3. A process according to claim 1, wherein water is introduced in liquid form.

4. A process according to claim 1, wherein water is introduced in the form of steam.

5. A process according to claim 1, wherein water is introduced in just the amount which corresponds to a water content in the range from 6.7 to 6.9% by weight in the vapors leaving the distillation at the top.

6. A process according to claim 1, wherein 0.1 to 5% by weight of water is introduced, relative to the crude liquid vinyl acetate.

7. A process according to claim 1, wherein the sidestream contains up to 8% by weight of ethyl acetate.

* * * * *